(12) United States Patent
Amarasinghe et al.

(10) Patent No.: US 8,042,541 B2
(45) Date of Patent: Oct. 25, 2011

(54) MASK BRACE AND MASK ASSEMBLY

(75) Inventors: Amal Shirley Amarasinghe, West Pennant Hills (AU); Robert Henry Frater, Lindfield (AU)

(73) Assignee: ResMed Limited, Bella Vista (AU)

( * ) Notice: Subject to any disclaimer, the term of this patent is extended or adjusted under 35 U.S.C. 154(b) by 1112 days.

(21) Appl. No.: 10/433,564

(22) PCT Filed: Dec. 7, 2001

(86) PCT No.: PCT/AU01/01578
§ 371 (c)(1),
(2), (4) Date: Nov. 5, 2003

(87) PCT Pub. No.: WO02/45784
PCT Pub. Date: Jun. 13, 2002

(65) Prior Publication Data
US 2004/0065328 A1    Apr. 8, 2004

(30) Foreign Application Priority Data
Dec. 7, 2000  (AU) ..................................... PR 1933

(51) Int. Cl.
*A62B 18/08*   (2006.01)
*A62B 18/02*   (2006.01)
*A62B 9/04*    (2006.01)
*A62B 18/00*   (2006.01)
*A62B 9/00*    (2006.01)

(52) U.S. Cl. ......... 128/207.11; 128/206.27; 128/206.21; 128/205.25; 128/202.27; 128/200.24

(58) Field of Classification Search ............. 128/206.27, 128/202.27, 203.29, 205.25, 206.12, 206.16, 128/206.17, 206.21, 206.24, 207.11
See application file for complete search history.

(56) References Cited

U.S. PATENT DOCUMENTS

| | | | | |
|---|---|---|---|---|
| 580,511 | A * | 4/1897 | Scheerer ................. | 128/203.29 |
| 787,828 | A * | 4/1905 | Clayton ................... | 128/203.29 |
| 2,011,733 | A * | 8/1935 | Shindel .................... | 128/206.24 |
| 2,079,581 | A | 5/1937 | Whipple | |
| 2,444,417 | A * | 7/1948 | Bierman .................. | 128/201.19 |
| 2,875,757 | A | 3/1959 | Galleher, Jr. | |
| 3,599,635 | A * | 8/1971 | Ansite ...................... | 128/206.28 |
| 3,977,432 | A * | 8/1976 | Vidal ........................ | 137/889 |
| 4,231,363 | A * | 11/1980 | Grimes ..................... | 128/205.25 |
| 4,630,604 | A | 12/1986 | Montesi | |

(Continued)

FOREIGN PATENT DOCUMENTS
DE     3927038    2/1991
(Continued)

OTHER PUBLICATIONS
Supplementary Partial European Search Report mailed Jul. 2, 2007 in European Application No. 01999401.1.

*Primary Examiner* — Justine Yu
*Assistant Examiner* — Annette Dixon
(74) *Attorney, Agent, or Firm* — Nixon & Vanderhye P.C.

(57) ABSTRACT

A patient mask assembly for positive pressure ventilation includes a brace (12) which clips to the mask and provides attachment locations (17) for headgear straps (14) in alternative positions to those attachment locations (17) which may be provided by the mask. The brace may also provide a mask stabilizing portion (20).

25 Claims, 5 Drawing Sheets

U.S. PATENT DOCUMENTS

| | | | |
|---|---|---|---|
| 4,944,310 A | 7/1990 | Sullivan | |
| 4,951,664 A * | 8/1990 | Niemeyer | 128/206.24 |
| 5,005,571 A | 4/1991 | Dietz | |
| 5,243,971 A | 9/1993 | Sullivan et al. | |
| 5,245,995 A | 9/1993 | Sullivan et al. | |
| 5,560,354 A | 10/1996 | Berthon-Jones et al. | |
| 5,617,849 A * | 4/1997 | Springett et al. | 128/206.24 |
| 5,647,357 A | 7/1997 | Barnett et al. | |
| 5,662,101 A * | 9/1997 | Ogden et al. | 128/205.25 |
| 5,687,715 A * | 11/1997 | Landis et al. | 128/207.18 |
| 5,921,239 A | 7/1999 | McCall et al. | |
| 5,953,848 A * | 9/1999 | Darnell et al. | 43/42.19 |
| 6,019,101 A | 2/2000 | Cotner et al. | |
| 6,119,693 A | 9/2000 | Kwok et al. | |
| 6,123,082 A | 9/2000 | Berthon-Jones et al. | |
| 6,192,886 B1 * | 2/2001 | Rudolph | 128/207.13 |
| 6,422,238 B1 | 7/2002 | Lithgow | |
| 6,491,034 B1 * | 12/2002 | Gunaratnam et al. | 128/204.18 |
| 6,513,526 B2 * | 2/2003 | Kwok et al. | 128/206.24 |
| 6,631,718 B1 * | 10/2003 | Lovell | 128/206.24 |
| 6,712,072 B1 * | 3/2004 | Lang | 128/206.27 |
| 6,789,543 B2 * | 9/2004 | Cannon | 128/207.18 |
| 2004/0025882 A1 * | 2/2004 | Madaus et al. | 128/206.27 |
| 2006/0174892 A1 | 8/2006 | Leksutin et al. | |
| 2007/0062537 A1 | 3/2007 | Chiesa et al. | |
| 2007/0101997 A1 | 5/2007 | Chiesa et al. | |

FOREIGN PATENT DOCUMENTS

| | | | |
|---|---|---|---|
| DE | 10035946 .9 | * | 6/2000 |
| EP | 1 892 006 A1 | | 2/2008 |
| FR | 270280 | | 12/1995 |
| GB | 2176404 A | | 12/1986 |
| JP | 51-29793 | | 8/1976 |
| JP | 3039303 U | | 4/1997 |
| JP | 2001-511035 A | | 8/2001 |
| JP | 2002-526180 A | | 8/2002 |
| WO | WO 98/012965 | | 4/1998 |
| WO | WO 99/061088 | | 12/1999 |
| WO | WO 2006/074273 A2 | | 7/2006 |

* cited by examiner

MASK BRACE AND MASK ASSEMBLY

BACKGROUND OF THE INVENTION

1. Field of the Invention

The invention relates to the configuration, fitting and operation of a mask suitable for the delivery of non-invasive positive pressure ventilation and for nasal CPAP treatment of sleep disordered breathing conditions such as obstructive sleep apnea.

2. Description of Related Art

Obstructive Sleep Apnea (OSA) is a disease characterized by excessive daytime sleepiness, loud snoring and daytime irritability. Other effects of OSA can include depression, high blood pressure, serious heart conditions, sexual problems, memory lapses, intellectual deterioration and morning headaches. The treatment of OSA by the application of nasal Continuous Positive Air Pressure (CPAP) was invented by Sullivan and is described in U.S. Pat. No. 4,944,310 (Sullivan, assignee ResMed Limited). The technique involves the application of a flow of pressurized breathable gas (typically room air) to either the nose or nose and mouth of a patient while they sleep. This technique is said to "splint" open the airways. Typical treatment pressures are in the range of 3 to 20 cm $H_2O$. Flows are up to approximately 200 L/min. Usually the flow of pressurized air is produced by a blower and delivered to the patient via a patient interface. The source of the air flow and patient interface are joined by a conduit Whilst there are other techniques for the treatment of OSA such as surgery, the use of CPAP has become the "gold" standard. For a particular patient the pressure which is needed to maintain open airways can vary throughout the night and vary on different nights. U.S. Pat. No. 5,245,995 (Sullivan and Lynch, assignee ResMed Limited) describes a method and device for varying the pressure in accordance with indications. For example, if the patient starts to snore, the pressure automatically increases, whilst in the absence of snoring the pressure automatically decreases.

Non-Invasive Positive Pressure Ventilation (NIPPV) is another form of treatment for breathing disorders. In its most basic form it involves a relatively higher pressure of gas being provided in the patient mask during the inspiratory phase of respiration and a relatively lower pressure or atmospheric pressure being provided in the patient mask during the expiratory phase of respiration. Typical treatment pressures are in the range of 3 to 30 cm $H_2O$.

In other NIPPV modes the pressure can be made to vary in a complex manner throughout the respiratory cycle. For example, the pressure at the mask during inspiration or expiration can be varied through the period of treatment, as disclosed in international PCT patent applications PCT/AU97/00631 (Berthon-Jones, assignee ResMed Limited) and PCT/AU99/00386 (Berthon-Jones, assignee ResMed Limited).

In this specification, any reference to CPAP treatment is to be understood as embracing all of the above-described forms of ventilatory treatment or assistance.

One of the earliest patient interfaces for providing CPAP treatment was constructed to include a fiberglass model of the patient's nose. The model was adhered to the patient's nose each night and removed each morning. An advantage of this patient interface included the customized fit which assisted in achieving a good seal between the patient interface and the patient's airways. However the use of adhesive to secure the mask was inconvenient and not desirable.

Another suitable patient interface is described in U.S. Pat. No. 5,243,971 (Sullivan and Bruderer, assignee University of Sydney) entitled "Nasal Mask for CPAP having Ballooning/Moulding Seal with Wearer's Nose and Facial Contours". This patent describes a nasal mask with a soft face-contacting portion and a rigid shell. The mask is held in position using headgear. The headgear is attached to the mask shell and passes around the back of the wearer's head. The patent depicts two sets of straps in the headgear. The first set comprised a pair of straps passing from the forehead region to the back of the head. The second set comprised a pair of straps passing from the nasal region of the mask to the back of the head.

Another known patient interface is the MIRAGE® nasal mask (by ResMed Limited). This nasal mask includes a pair of headgear attachment points in the nasal region of the mask shell and a forehead support which includes another pair of headgear attachment points. The forehead support to this mask is the subject of U.S. Pat. No. 6,119,693 (Kwok, Matchett & Grant, assignee ResMed Limited). The headgear comprises a single piece of a soft, flexible composite fabric with a generally triangular back portion and four straps. The four straps comprise a pair of upper straps and a pair of lower straps connecting to the headgear attachment points on the forehead support and nasal mask shell respectively. At the end of each strap is secured a piece of hook and loop fastening material such as Velcro™ which, in use, passes through a headgear attachment point and fastens on corresponding loop material on the strap. The generally triangular back portion engages the skull in the region of the occiput. The fabric stretches under a load. The base of the triangle is positioned near and generally in line with the upper straps.

Some patients open their mouths during sleep which means that they may not receive the benefit of nasal CPAP due to mouth leaks. Various solutions have been proposed for this problem. One solution is taught in U.S. Pat. No. 6,123,082 (Berthon-Jones, assignee ResMed Limited), whereby the lips are held closed. Another solution is to use a mask which covers both the nose and mouth of the patient. An example of a mouth and nasal mask is described in U.S. Pat. No. 5,560,354 (Berthon-Jones, Calluaud, Lynch & Hely, assignee ResMed Limited).

Another suitable mask system is the MIRAGE® full face mask (by assignee ResMed Limited). The MIRAGE® full face mask and headgear is illustrated in FIG. 1 . Suitable headgear for this mask is constructed from a composite material of nylon, neoprene and hook and loop material. The headgear similarly comprises a pair of upper and a pair of lower straps and a generally triangular back portion. The upper strap has a total length of approximately 610 mm, The straps have an approximate width. of 25 mm, however the upper strap has an approximate width of 19 mm. The triangular region has a base of approximately 15.5 cm and two equal sides of approximately 11 cm. The upper and lower straps are approximately 192 mm apart. In addition, the headgear includes a quick release mechanism as described by U.S. Pat. No. 6,422,238 (Lithgow, assignee ResMed Limited). The quick release mechanism provides a "rip cord" which can be pulled upon to separate the headgear and hence remove the mask in an emergency. When the headgear is positioned on the patient's head, the quick-release mechanism is situated at the back of the head and the cord runs through loops towards the front of the mask system.

Patient interface arrangements include nasal masks, nose and mouth masks, nasal prongs and nasal pillows. In all forms of patient interface used with CPAP for treating sleep disordered breathing, there is a need to counterbalance the force of the pressurized air and to correctly position the interface. Since the patient must sleep with this interface, it is important that it be comfortable. From the manufacturing and distribution channel perspectives, it is advantageous if one size of headgear fits a large range of head shapes and sizes.

Other examples of prior art headgear and mask shells have configurations which are different to those depicted in U.S. Pat. No. 5,243,971 and used in the MIRAGE® nasal mask and MIRAGE® full-face mask in so far as they incorporate a different number of headgear straps or differ in the placement of the head strap attachment points or both. This variety of mask configurations is required to address the biological variability existing between users, each user having a unique facial and head shape. However no one mask system involving headgear and fixed point strap attachment points offers continuous variability in placement. As a result, when selecting from a range of mass produced mask and headgear systems, in the majority of cases the selection will represent a compromise for the user where a balance must be struck between comfort and the achievement of a secure fit and good seal between the mask and the user.

An approach to headgear attachment which allows for great variability in head strap number and attachment position to the mask would yield great benefits to the user in terms of comfort and function, to the mask system manufacturer in terms of facilitating the opportunity to easily experiment with different mask positions and headgear configurations while moving towards the desirable objective of rationalising manufacturer and supplier inventory.

It should be noted that while there are many mask and headgear arrangements available for ventilators, respirators, aviator masks and other breathing apparatus, generally these may not be suitable for use in the treatment of sleep disordered breathing because they are not sufficiently comfortable to allow the patient to sleep.

The present invention is directed towards providing a method of configuring a mask and a mask for use in the treatment of sleep disordered breathing which improves patient comfort, is long lasting and fits a wide range of head shapes and sizes.

SUMMARY OF THE INVENTION

The present invention relates to an improvement to the method and apparatus for the positioning and attachment of headgear to a patient interface such as a mask.

The invention includes the incorporation of a brace into the mask which is independent of the mask shell, said brace being adapted in use to be held in a substantially fixed position relative to the mask shell and to accommodate the attachment of at least part of the headgear.

The present invention enables the attachment points for headgear to be determined and varied in a physical or temporal sense independently of the mask shell configuration.

The invention broadly resides in a brace for a patient airway interface, the brace being shaped so as to be retainingly engageable with the interface and providing at least one formation for engagement with a headgear member.

Preferably the brace includes an elongate member shaped so as to be engageable by formations on said interface.

The invention also broadly resides in a brace for a patient airway interface, the brace being shaped so as to be retainingly engageable with the interface, the brace further including a formation disposed for engagement with the patient's forehead.

DESCRIPTION OF PREFERRED EMBODIMENTS OF THE INVENTION

Figure 1:
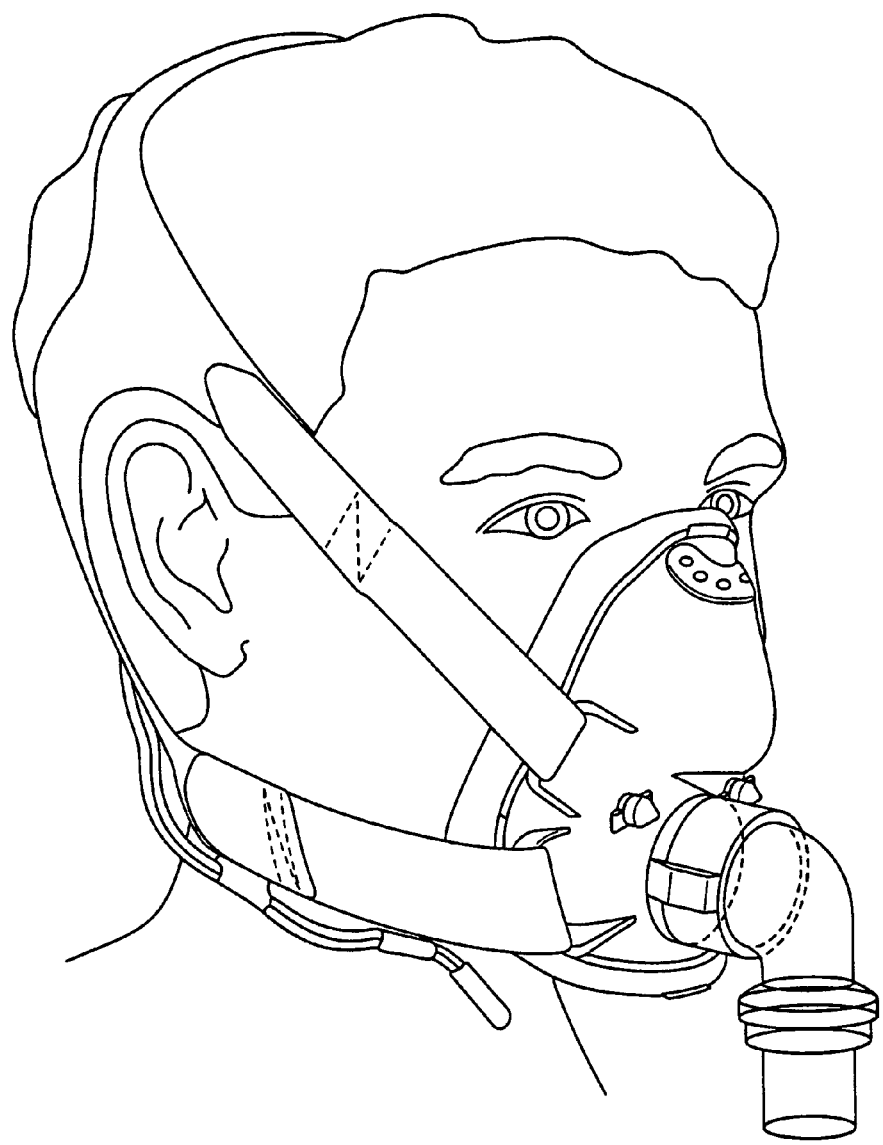
FIG. 1 shows a prior art full-face mask system located on a user's face.
Figure 2:
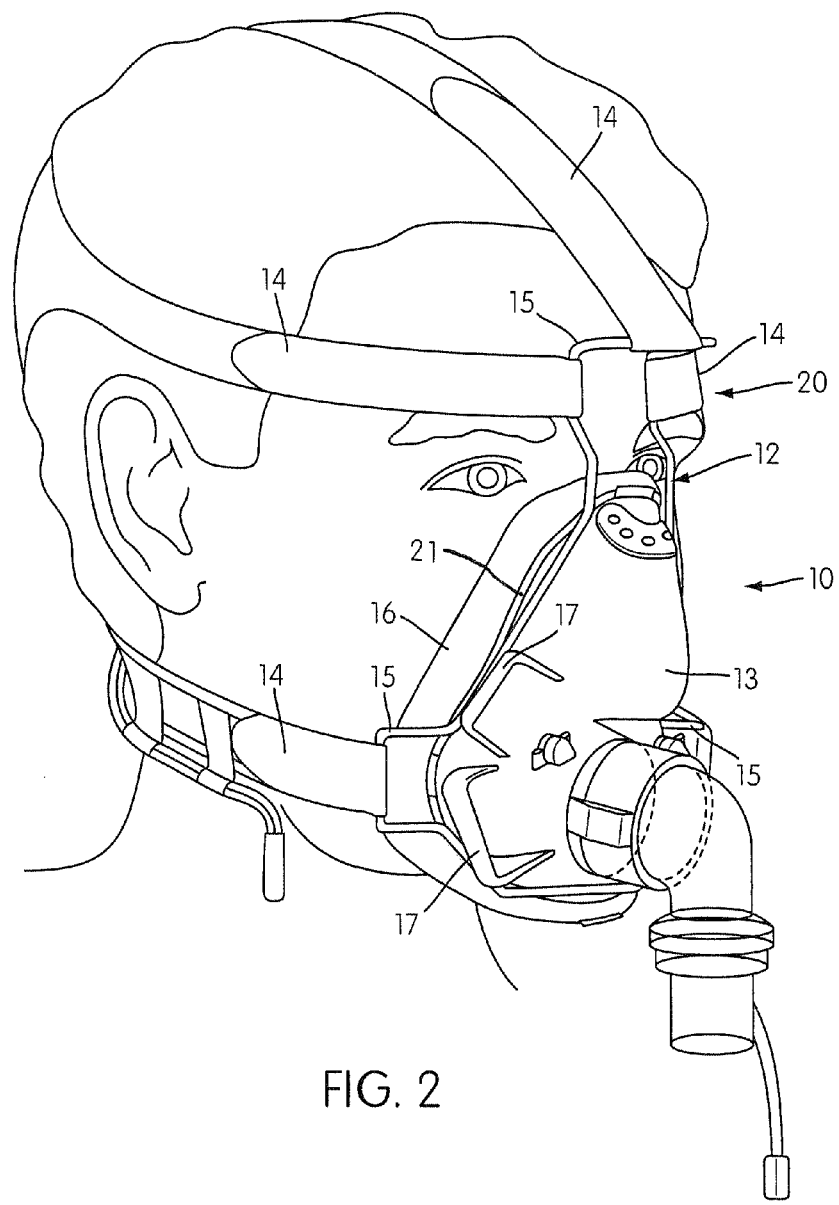
FIG. 2 shows a mask system incorporating a brace according to the present invention located on a user's face.

FIG. 2 shows a mask system 10 incorporating the present invention consisting of a brace 12, mask shell 13, headgear straps 14, brace head strap attachment points 15, mask cushion 16 and mask shell headgear attachment points 17.

It will be immediately apparent that the headgear attachment points 17 of the mask shell are superfluous in this embodiment of the present invention so far as concerns their original intended role as attachment points for the headgear. This is because the headgear attachment points of the brace serve the requisite purpose independently of any attachment point of the mask shell. Nevertheless because it is intended that the brace assume a fixed predetermined position with respect to the mask shell, existing mask shell headgear attachment points 17 can serve as retaining formations for the brace.

While the brace depicted in FIG. 2 has provision for attaching five headgear straps, the brace may be configured so as to receive any suitable number. The present invention envisages the brace assuming a substantially constant position relative to the mask shell when the mask assembly is properly located on the user. It may be configured to receive at least as many headgear straps as are required for a particular headgear configuration or alternatively may have less than or more headgear attachment points with respect to any particular headgear configuration.

The versatility of the present invention will be immediately apparent to those skilled in the art in that for any given mask shell, it is possible to configure a brace so as to receive the requisite number of headgear straps and to locate the brace headgear attachment points in such locations as to allow a user to choose between a variety of headgear configurations. This versatility allows the user to optimise their choice of headgear as the particular requirements may dictate so as to achieve the requisite mask seal and comfort.

A user may be supplied with a number of braces each with a different number of headgear attachment points or at least having a set number of headgear attachment points positioned in a variety of configurations with respect to the mask shell in order that a suitable choice may be made.

In an embodiment of the invention, the brace is designed so as to achieve a "clip fit" on an existing mask frame as previously described.

Figure 3:
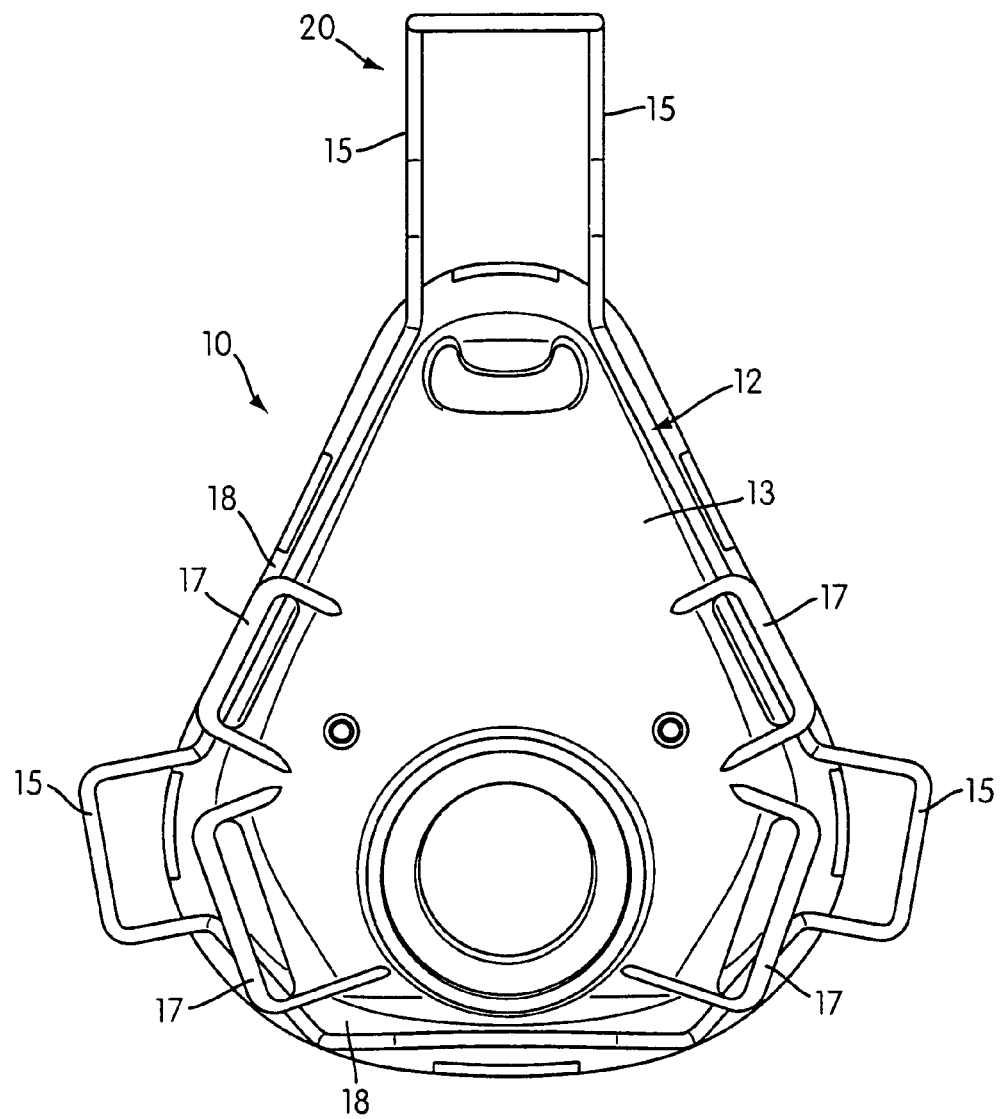
FIG. 3 shows a. brace according to the present invention located on a mask shell.
Figure 4:
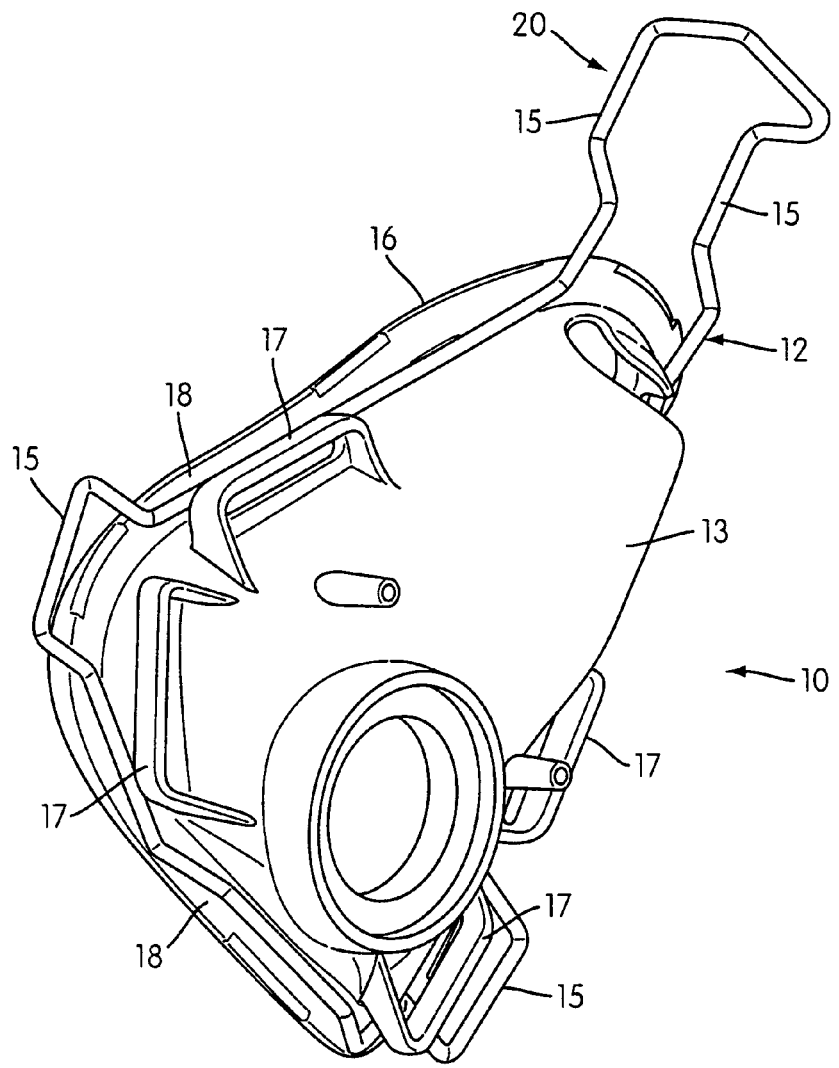
FIG. 4 shows another view of the brace and mask of FIG. 3.

FIG. 3 illustrates a clip fit arrangement in which a brace 12 is fitted between the existing mask frame headgear attachment points 17 and the mask shell outer surface, in this case the peripheral flange portion 18. Where headgear strap attachment points 17 are provided for on the mask shell they may be used in conjunction with some or all of the headgear strap attachment points 15 of the brace 12 thereby providing further flexibility in the configuration.

In an alternative embodiment of the invention (not illustrated) suitable engagement points may be created within the mask shell so as to receive the brace, such attachment points being designed so as not to be suitable for attaching headgear straps.

Because of the versatility offered by the brace of the present invention, it also offers the possibility for incorporating a mask stabilising feature independent of or in addition to the inclusion of the headgear attachment points. An example of such a stabilizing feature is illustrated in the accompanying drawings in the form of a forehead stabilising section 20. The stabilizing portion 20 takes the form of a portion of the brace extending clear of the mask shell so as to provide an elevated engagement point and/or to contact a portion of the user's face, in this case the forehead. The malleability of the wire used to form the brace allows the position of the stabilizing portion to be adjusted for individual patients. In FIG. 2 it can be seen that the forehead stabilising portion 20 is in near contact or contact with the user's forehead thereby limiting movement of the accompanying mask frame and mask cushion towards to the user's face in the region of the nasal bridge. This stabilising feature is achieved due to the relatively rigid engagement of the brace in relation to the mask shell.

Figure 5:
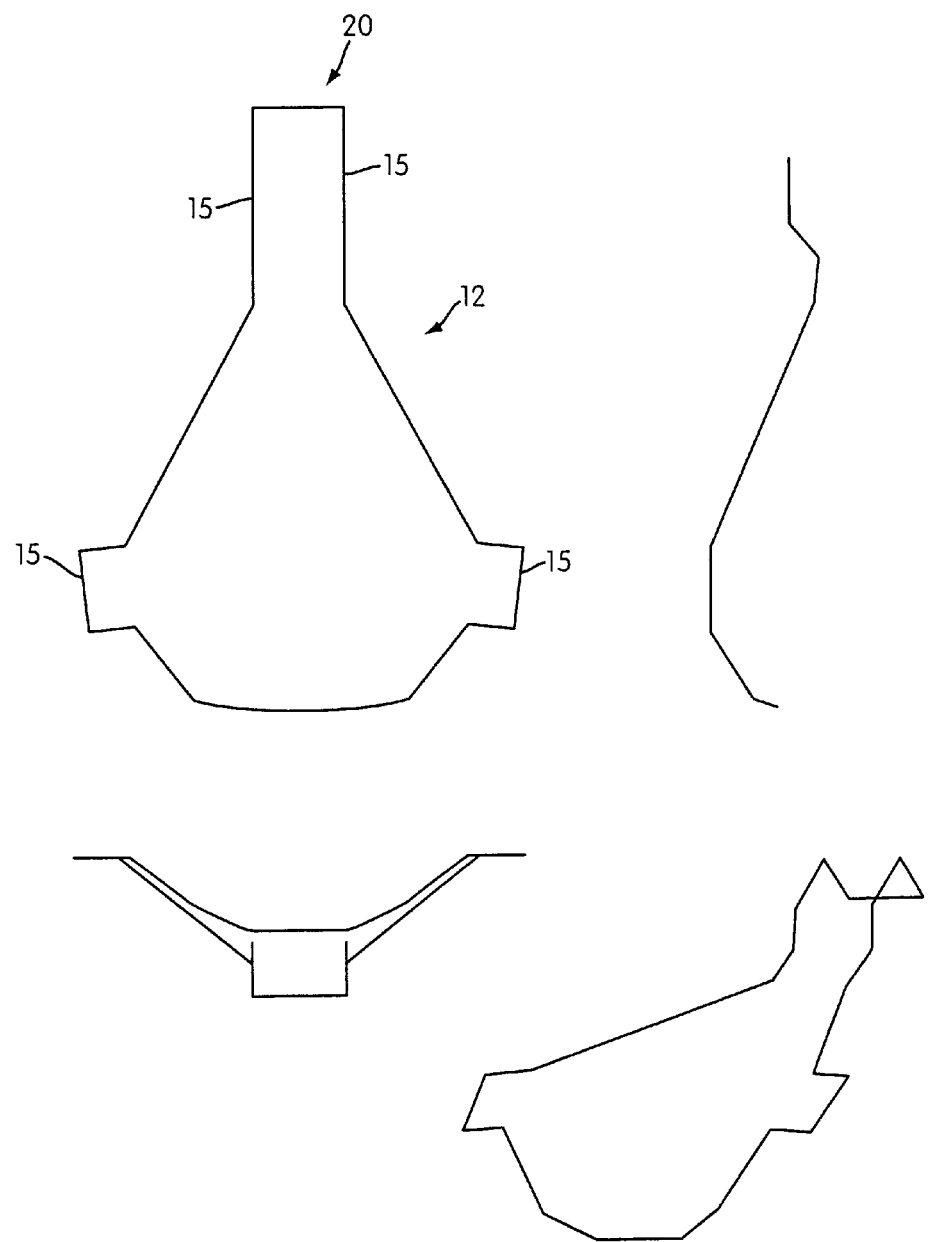
FIG. 5 shows a brace according to the present invention.

FIG. 5 shows schematically a version of a brace according to the present invention suitable for use with a MIRAGE® full-face mask system by the present applicant. The brace is constructed of 2.5 mm gauge mild steel wire butt-welded so as to assume a continuous form. The wire is bent to the appropriate configuration using standard wire bending techniques which may include automated bending by way of a suitably programmed NC wire bending machine.

Preferably the resulting brace is powder coated so as to provide for a corrosive resistant and easily cleaned surface.

Mask shells are typically molded from polycarbonate or similar material. Such a construction technique requires a relatively expensive molding tool. This means that it is expensive for the manufacturer to change the location of the headgear attachment points if they are molded into the mask shell. In contrast it is relatively cheap to configure and manufacture a brace according to the present invention.

The brace is easily hand fitted to the mask frame and clip set in place as previously described. This manoeuvre being easily achieved by hand, in view of the inherent malleability of the brace material. It is clear that an alternative embodiment could be configured so as to adapt the brace to be received by brace receiving features in a mask frame.

It is also intended that the brace could be configured so as to engage brace receiving features that may be provided by a mask cushion clip 21. In this way the brace may be accurately and securely positioned relative to the mask frame while serving to secure the cushion clip and cushion to the mask frame. The brace engaging feature may be located on the brace with a reciprocal feature on the mask shell or alternatively may be a separate component that engages the brace and the mask shell. The brace receiving features may either extend around the outer circumference of the mask frame surrounding and securing the mask cushion or may pass through apertures provided for in the mask frame.

The method and mask assembly of the present invention provide further advantages such as allowing for the inclusion of other accessories that would be of benefit to the user, such as provision for holding or attaching a gastro-nasal tube or a sensor for measuring physiological parameters of the user, attaching a tube for the provision of a supplemental gas or pharmaceuticals, or attachment of other accessories such as a device for preventing or inducing the passage of air through the mouth such as is described and depicted in U.S. Pat. No. 6,123,082 (Berthon-Jones, assignee ResMed Limited).

Other benefits of the invention include the ability to disassemble the headgear from the mask while the headgear is engaged with the brace without affecting strap length adjustment in order that the mask shell and cushion may be washed. The benefit of this is that the brace and headgear assembly may be re-attached to the mask frame without requiring the re-adjusting of the strap length.

This is because once the brace is located in the predetermined position relative to the mask frame, the head strap position relative to the mask frame will resume the position it was in at the time that the brace was removed from the mask shell.

By making the mask brace of a malleable material, such as is described above in relation to the preferred embodiment, it will be appreciated that a user can make some adjustment to the position of the headgear retaining portion or the mask stabilising feature or both so as to meet particular needs. This opportunity to make such adjustments allows for rapid tailoring of the mask assembly to a user's particular requirements.

While the preferred embodiment includes description of a mask brace having a clip fit to the mask shell, it is envisaged that the brace might be attached to the mask shell by other means such as a hook and loop system like Velcro™ or other suitable means. Preferably the attachment means achieves a consistent support of the brace relative to the mask frame while located but also allowing for a relatively easy disassembly of the two components in order to facilitate the achievement of other benefits that come with the present invention.

The present invention is particularly suitable for accommodating asymmetrical mask configurations as may be required by users such as those with facial palsy. For example, the present invention allows for the individual configuration of asymmetrical head strap attachment points and use of asymmetrical mask cushions with standard mask frames.

The invention claimed is:

1. A patient airway interface assembly, comprising:
    a mask shell configured to cover at least the patient's nose, the mask shell including a first set of headgear connection points;
    a cushion attached to the mask shell and configured to sealingly engage the patient's face; and
    a brace comprising an elongate member configured to engage the mask shell at a fixed predetermined position with respect to the mask shell, wherein the brace is shaped so as to be retainingly engageable with and detachable from the mask shell and includes a second set of headgear connection points, the elongate member being shaped so as to be engageable by formations on the mask shell, wherein the elongate member is configured to extend around the entire perimeter of the mask shell.

2. A patient airway interface assembly according to claim 1, wherein the mask shell is configured to cover the patient's nose and mouth and at least a portion of the brace is configured to extend under the patient's chin.

3. A patient airway interface assembly according to claim 1, wherein the elongate member comprises a continuous form.

4. A patient airway interface assembly according to claim 1, wherein the elongate member comprises a wire.

5. A patient airway interface assembly according to claim 4, wherein the wire is formed of metal.

6. A patient airway interface assembly according to claim 5, wherein the wire comprises a mild steel wire.

7. A patient airway interface assembly according to claim 1, wherein the brace is rigidly engaged with the mask shell.

8. A patient airway interface assembly according to claim 1, wherein the elongate member is continuously deformable by hand.

9. A patient airway interface assembly according to claim 1, wherein the elongate member is malleable.

10. A patient airway interface assembly according to claim 1, wherein the formations on the mask shell comprise the first set of headgear connection points.

11. A patient airway interface assembly according to claim 10, wherein the formations on the mask shell further comprise a peripheral flange of the mask shell.

12. A patient airway interface assembly according to claim 10, wherein the formations on the mask shell further comprise a cushion clip that is configured to secure the cushion to the mask shell.

13. A patient airway interface assembly according to claim 12, wherein the brace engages the mask shell and the cushion clip to secure the cushion clip to the mask shell.

14. A patient airway interface assembly according to claim 1, wherein the elongate member includes a portion disposed, in use, in the region of the patient's forehead.

15. A patient airway interface assembly according to claim 14, wherein at least one of the second headgear connection points is located in the portion disposed in the region of the patient's forehead.

16. A patient airway interface assembly according to claim 1, wherein the first set of headgear connection points provide a different headgear alignment from that provided by the second set of headgear connection points.

17. A patient airway interface assembly, comprising:
a rigid shell configured to cover the nose and the mouth of the patient, the shell comprising a first side configured to face the patient in use and a second side opposite the first side, the first side comprising a peripheral flange extending around a perimeter of the shell, the second side comprising two headgear strap attachment formations configured to attach straps of a headgear to the second side of the shell, the two headgear strap attachment formations being provided on opposite sides of a central axis of the shell and integrally formed with the shell, the shell further comprising an aperture provided between the two headgear strap attachment formations and configured to receive an elbow;
a cushion attached to the peripheral flange, the cushion being configured to form a seal with the patient's face in use;
an elongate, continuous member extending around the perimeter of the shell, the elongate, continuous member being rigidly engaged with the mask shell between the peripheral flange and the two headgear strap attachment formations and assuming a substantially constant position relative to the mask shell, wherein the elongate, continuous member is shaped so as to be retainingly engageable with and detachable from the mask shell.

18. A patient airway interface assembly according to claim 17, wherein the elongate, continuous member is malleable.

19. A patient airway interface assembly according to claim 17, wherein the elongate, continuous member is removably detachable from the shell.

20. A patient airway interface assembly according to claim 17, further comprising a cushion clip configured to secure the cushion to the shell.

21. A patient airway interface assembly according to claim 20, wherein the elongate, continuous member engages the shell and the cushion clip to secure the cushion clip to the shell.

22. A patient airway interface assembly according to claim 17, wherein the elongate, continuous member includes a portion disposed, in use, in the region of the patient's forehead.

23. A patient airway interface assembly according to claim 22, wherein the portion disposed in the region of the patient's forehead comprises at least one headgear strap attachment formation.

24. A patient airway interface assembly according to claim 17, wherein the elongate, continuous member is continuously deformable by hand.

25. A patient airway interface assembly according to claim 17, wherein the elongate, continuous member comprises at least two headgear strap attachment formations that provide a different headgear alignment from that provided by the two headgear strap attachment formations of the shell.

* * * * *